United States Patent
Nakanishi

[11] Patent Number: 6,099,308
[45] Date of Patent: Aug. 8, 2000

[54] DENTAL HANDPIECE WITH DUST CONTROL MECHANISM

[75] Inventor: Takasuke Nakanishi, Kanuma, Japan

[73] Assignee: Nakanishi, Inc., Tochihi-Ken, Japan

[21] Appl. No.: 09/425,250

[22] Filed: Oct. 25, 1999

[30] Foreign Application Priority Data

Oct. 27, 1998 [JP] Japan ................... 10-304975

[51] Int. Cl.$^7$ ........................ A61C 1/05
[52] U.S. Cl. ........................ 433/115
[58] Field of Search .................. 433/115, 116, 433/132

[56] References Cited

U.S. PATENT DOCUMENTS 5,252,065  10/1993  Nakanishi ................ 433/115
5,423,678   6/1995  Nakanishi ................ 433/115
5,692,903  12/1997  Nakanishi .............. 433/115 X

*Primary Examiner*—Nicholas D. Lucchesi
*Attorney, Agent, or Firm*—Keil & Weinkauf

[57] ABSTRACT

A dental handpiece is disclosed which has a housing having a wall, a bur sleeve for receiving and holding a dental tool therein, a bearing for rotatably supporting the bur sleeve, a rotary dust control member fixed on the bur sleeve, and a stationary dust control member forming a gap in cooperation with the rotary dust control member and the wall of the housing for preventing entry of contaminants inside the housing. The stationary dust control member is attached to the bearing.

10 Claims, 3 Drawing Sheets

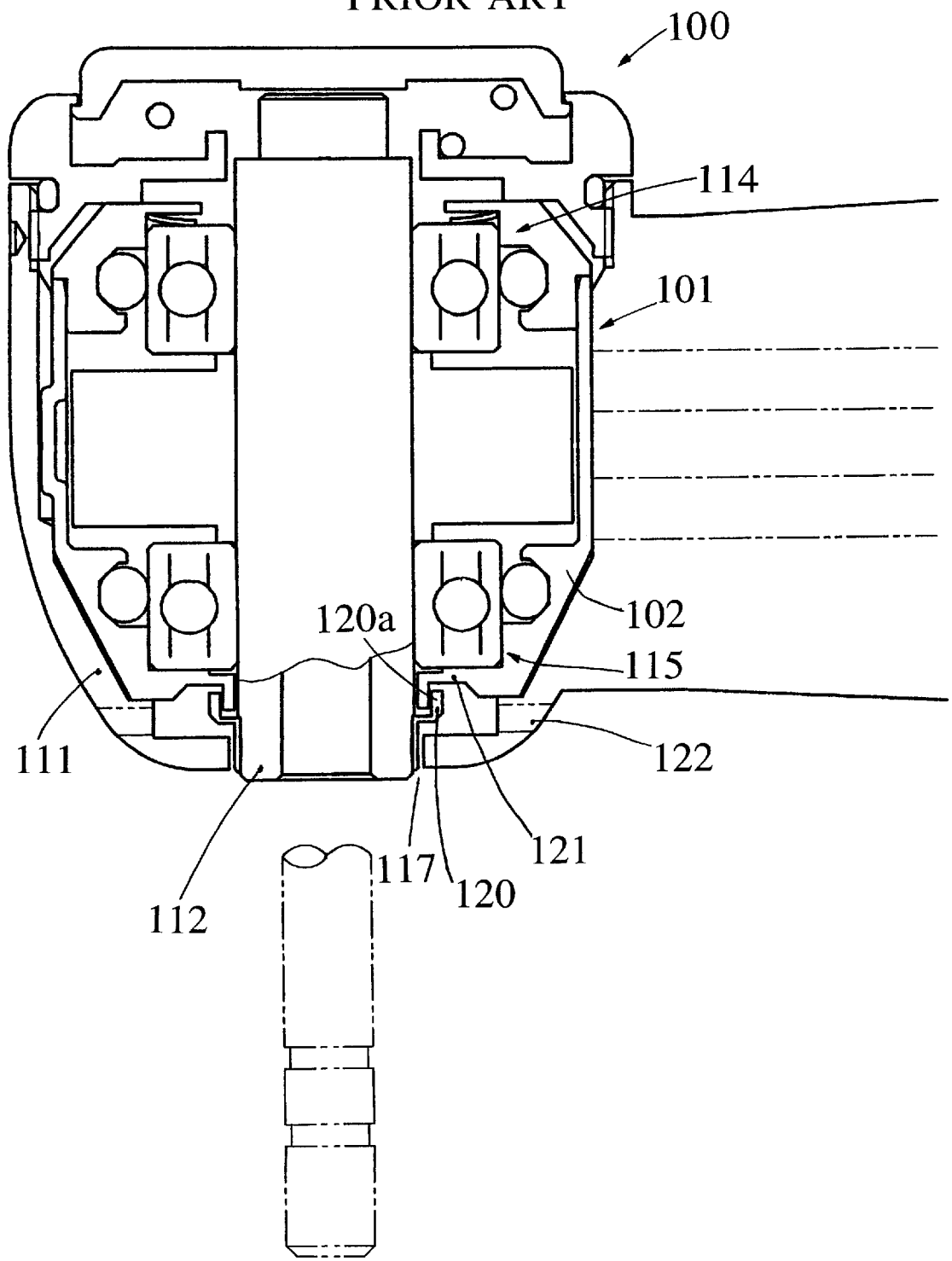

DENTAL HANDPIECE WITH DUST CONTROL MECHANISM

FIELD OF THE INVENTION

The present invention relates to a dental handpiece, in particular a dental handpiece having a mechanism for preventing intrusion of contaminants, such as debris, into a bearing in the handpiece.

BACKGROUND OF THE INVENTION

A dental handpiece has a bur sleeve for transmitting torque to a dental tool. It is known that rotation of the bur sleeve creates negative pressure inside the handpiece to cause suction of contaminants, such as debris generated during treatment, through an insertion port for a dental tool into the interior of the handpiece. The sucked contaminants may intrude further to a bearing supporting the bur sleeve and located in the proximity of the insertion port, to thereby damage the bearing races and adversely affect smooth rotation of the bearings.

In order to overcome these problems, there is known to provide a bearing seal or a bearing shield in the form of a simple annular plate. The bearing shield engages at one end a groove provided on one of the outer and inner rings of a bearing, and extends toward the other of the rings to cover the bearing. However, the gap between the free end of the shield and the bur sleeve may allow entry of contaminants into the bearing, and thus sufficient blocking effect cannot be achieved.

There have also been proposed dental handpieces having a dust control mechanism. An example of such handpieces is described below with reference to FIG. 3.

FIG. 3 illustrates head 100 of a conventional, angle-type handpiece having a dust control mechanism. The head 100 is of a cartridge type, and is composed of a head body 111 and a cartridge 101 detachably accommodated in the body 111. The cartridge 101 is, in turn, mainly composed of a socket 102, a bur sleeve 112 partly inserted into the socket 102, and upper and lower ball bearings 114 and 115 supporting the bur sleeve 112. The cartridge 101 is fit in the head body 111, with the bur sleeve 112 projecting through a tool insertion port 117.

The dust control mechanism of this handpiece includes a rotary dust control disc 120 fixed on the bur sleeve 112 near the distal end thereof, a stationary dust control disc 121 formed as an extension of the socket 102, and some discharge ports 122 located in the vicinity of the tool insertion port 117. The rotary disc 120 has a flange portion 120a defining a gap between the flange portion and the bur sleeve 112. The stationary disc 121 is inserted into the gap from above the flange portion 120a, to form gaps like a labyrinth.

When the bur sleeve 112 is rotated, negative pressure is created inside the head 100, which causes debris generated during treatment to enter the head 100 through the gap between the tool insertion port 117 and the bur sleeve 112. However, the rotary and stationary discs 120 and 121 prevent the debris from intruding into the ball bearing 115 by physically hitting the debris away or by creating the centrifugal force in the labyrinth, so that the debris is discharged out of the handpiece through the discharge ports 122.

The conventional dust control means provides sufficient advantages in prevention of dust intrusion into the handpiece. However, since the stationary disc 121 is not formed as an independent part, but formed integrally with the bulky socket 101, exchange of the disc 121, when damaged, is not convenient.

There is also known another type of dental handpieces with a dust control mechanism, wherein a stationary dust control disc is formed as an independent part and screwed onto the head. This structure, however, is complex, causing decrease in productivity.

SUMMARY OF THE INVENTION

It is therefore an object of the present invention to provide a dental handpiece having dust control means which excellently prevent intrusion of contaminants into the bearing.

It is another object of the present invention to provide a dental handpiece having dust control means which can be exchanged easily and conveniently when damaged.

It is another object of the present invention to provide a dental handpiece having dust control means which is simple in structure yet provides excellent and convenient attachment.

According to the present invention, there is provided a dental handpiece comprising a housing having a wall, a bur sleeve for receiving and holding a dental tool therein, a bearing for rotatably supporting said bur sleeve, a rotary dust control member fixed on said bur sleeve, and a stationary dust control member forming a gap in cooperation with said rotary dust control member and the wall of the housing for preventing intrusion of contaminants into the housing, wherein said stationary dust control member is attached to said bearing.

With this structure, even when the contaminants such as debris enter the interior of the handpiece through the tool insertion port, the rotary dust control member and the stationary dust control member cooperate to prevent the contaminants from intruding into the bearing. Thus, the bearing is protected from being damaged with the contaminants.

Since the stationary dust control member is attached to the bearing, the structure of the handpiece is simplified. Accordingly, the stationary dust control member, when damaged, can be exchanged conveniently.

In addition, the bearing on which the stationary dust control member is mounted, does not require special processing, but conventional bearings having a groove for a bearing shield may be used as the bearing of the present invention. Thus, the present invention allows use of the existing parts to increase productivity of the handpieces.

BRIEF DESCRIPTION OF THE DRAWINGS

The present invention will now be explained with reference to the attached drawings:

FIG. 3 is a cross-sectional view of a head of a conventional dental handpiece, wherein the stationary dust control disc is formed as an extension of a socket.

DETAILED DESCRIPTION OF PREFERRED EMBODIMENTS

In the figures, embodiments of the present invention are illustrated as an angle-type dental handpiece, but the present invention is not limited thereto and may be applied to a straight-type dental handpiece as well._

Figure 1:
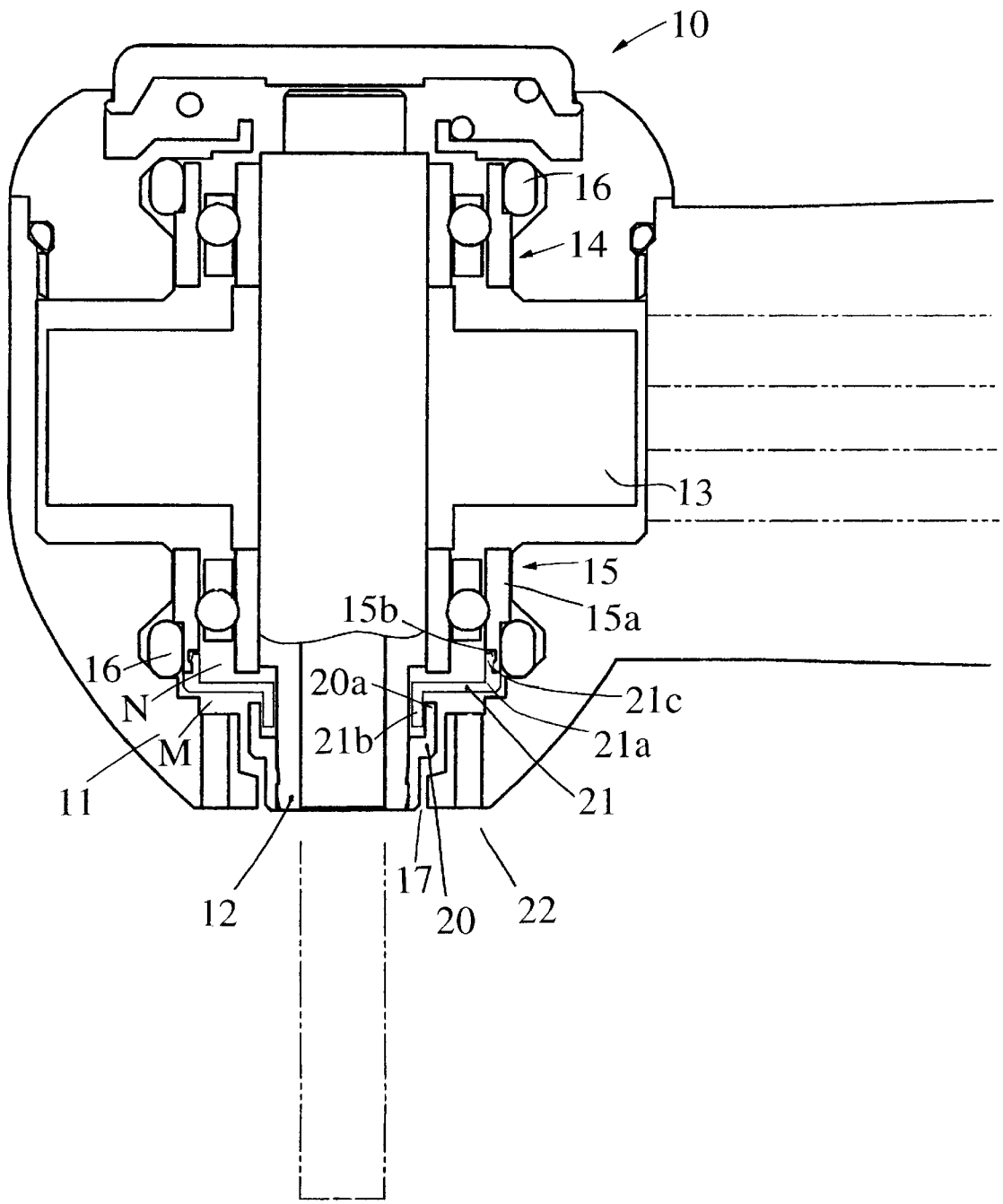
FIG. 1 is a cross-sectional view of a head of a dental handpiece according to an embodiment of the present invention.

FIG. 1 illustrates a dental handpiece of the present invention having head 10 at its distal end portion. The head 10 includes head housing 11, which accommodates bur sleeve 12 for receiving and holding a dental tool therein, rotor 13 for rotationally driving the bur sleeve 12, and upper and lower bearings 14, 15 rotatably supporting the bur sleeve 12. The head housing 11 has a tool insertion port 17, through which the distal end of the bur sleeve 12 is exposed to receive the dental tool in the sleeve 12. The rotor 13 is fixed on the outer surface of the bur sleeve 12 between the upper and lower bearings 14 and 15. The upper and lower bearings 14, 15 are ball bearings, each supported directly by the housing 11 via O-ring 16.

The lower bearing 15 has an outer ring 15a, which has a groove 15b for the purpose to be discussed later. The groove 15b extends circumferentially along the inner surface of the outer ring 15a in the lower portion thereof in this embodiment.

The head 10 also accommodates a dust control mechanism, which includes a rotary dust control disc 20 fixed on and rotated with the bur sleeve 12, a stationary dust control disc 21 attached to the lower bearing 15, and dust discharge ports 22 arranged near the tool insertion port 17. In this embodiment, the stationary dust control disc 21 is attached to the outer ring 15a of the lower bearing 15.

The rotary dust control disc 20 is generally an annular member securely fixed on the outer surface of the bur sleeve 12 at the tool insertion port 17. The disc 20 has in its upper portion a flange 20a defining an annular space around the bur sleeve 12.

The stationary dust control disc 21 is generally an annular member having upper and lower annular flanges 21a and 21b, respectively. The upper flange 21a has a hook 21c on its outer surface, which is a stepped portion extending along the entire periphery of the upper flange 21a. The hook 21c fits in the groove 15b on the outer ring 15a of the bearing 15, so that the disc 21 is attached to and depends from the outer ring 15a.

The lower flange 21b of the disc 21 is inserted into the gap between the outer surface of the bur sleeve 12 and the inner surface of the flange 20a of the rotary disc 20, and arranged in close proximity with, but slightly spaced from the bur sleeve 12 and the flange 20a to form a labyrinth.

In this arrangement, the disc 21 defines space M between the outer surface of the disc 21 and the inner surface of the housing 11, and space N between the inner surface of the disc 21 and the lower side of the bearing 15.

The dust discharge ports 22 extend through the head housing 11 in the direction substantially parallel to the bur sleeve 12 to connect space M defined in the housing 11 to outside. In this embodiment, a plurality of dust discharge ports 22 are arranged around the tool insertion port 17 at appropriate circumferential intervals.

In operation, air is supplied to the handpiece to drive the rotor 13, which in turn rotationally drives the bur sleeve 12 to give torque to the dental tool held therein. The rotation of the bur sleeve 12 generates negative pressure in the head housing 11, which causes contaminants such as debris to be sucked into the space M in the housing 11 through the tool insertion port 17. However, the rotary disc 20 and the stationary disc 21 physically block the bearing 15 against the contaminants by hitting away the contaminants on their surfaces. In addition, the discs 20 and 21 also cooperate to generate centrifugal forces in the labyrinth around the discs to prevent the contaminants from intruding into the space N. Therefore, the contaminants sucked into the space M cannot reach the bearing 15, and discharged through the discharge ports 22. Therefore, the bearing race of the bearing 15 is protected from being damaged with the contaminants.

Figure 2:
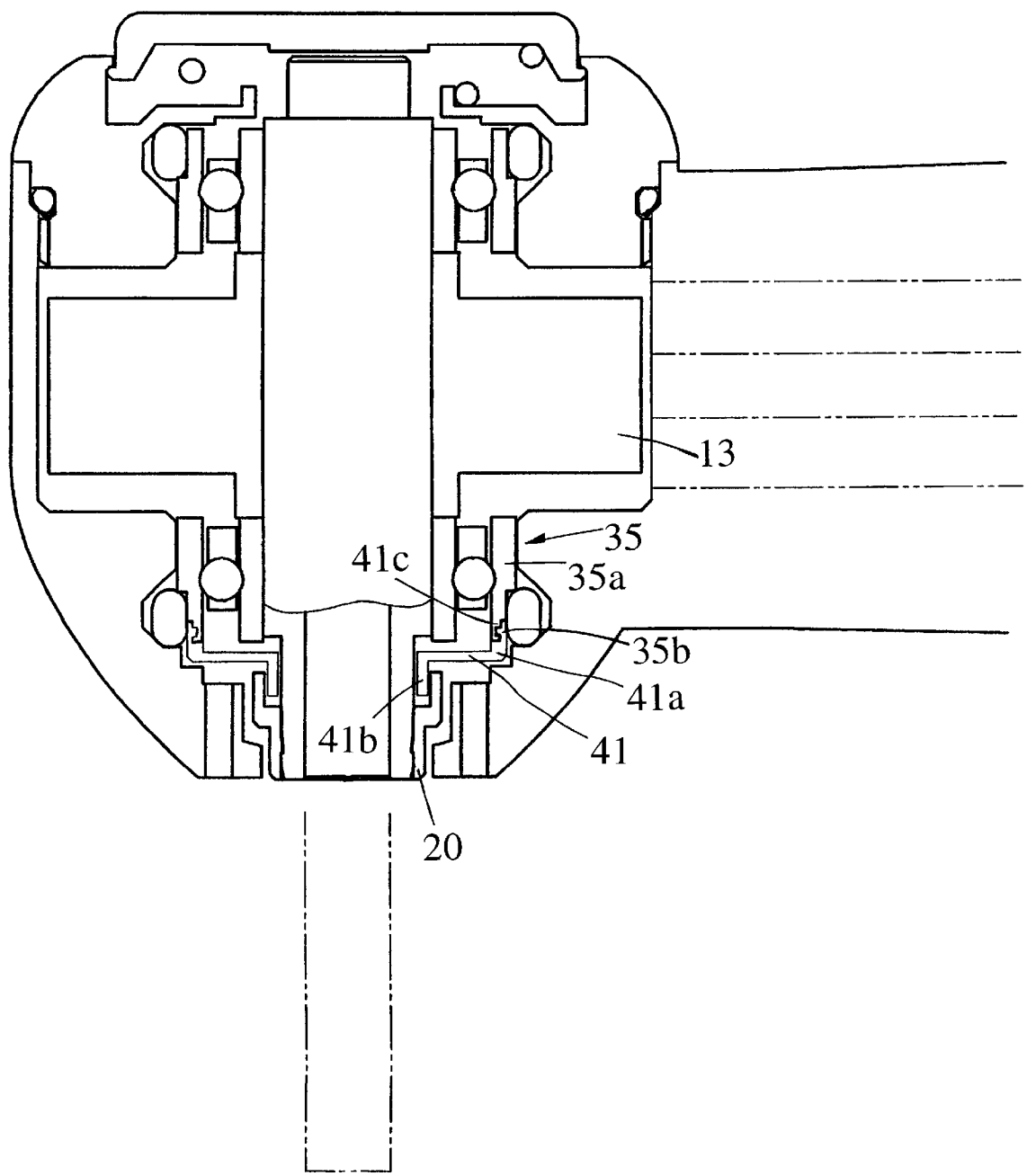
FIG. 2 is a cross-sectional view of a head of a dental handpiece according to another embodiment of the present invention.

FIG. 2 illustrates another embodiment of the present invention, wherein the same parts as in the first embodiment are designated by the same reference numerals.

The embodiment in FIG. 2 differs from the first embodiment in that the stationary disc 41 is attached to the outer surface of the outer ring 35a of the lower bearing 35. Specifically, the lower bearing 35 has an outer ring 35a, which has a groove 35b extending circumferentially along the outer surface thereof in the lower portion of the outer ring 35a. The stationary dust control disc 41 has upper and lower annular flanges 41a, 41b, and the upper flange 41a has a hook 41c on its inner surface. The hook 41c is a stepped portion extending along the entire periphery of the upper flange 41c. The hook 41c on the stationary disc 41 fits in the groove 35b on the outer ring 35a of the bearing 35, so that the disc 41 is attached to and depends from the outer ring 35a.

The operation of the second embodiment is the same as that of the first embodiment, so that it is not discussed further.

While the invention has been particularly shown and described with reference to the preferred embodiments thereof, it will be understood by those skilled in the art that various changes and modifications may be made in the present invention. For example, although the attachment of the stationary disc to the bearing outer ring is achieved by the hook on the disc and the groove on the bearing outer ring, it is understood that the hook may be provided on the bearing outer ring, and the groove may be provided on the disc. Any positional combinations of the hook and the groove are possible as long as the hook faces the groove to achieve the desired connection therebetween.

It is not necessary that the groove is newly provided. For example, a bearing which has been provided with a groove for a conventional bearing shield may be used as the lower bearing for supporting the stationary disc. In this case, the hook on the stationary disc is shaped to complementarily match the contour of the groove on the bearing.

In the embodiments discussed above, both hook and groove extend along the entire periphery of the disc or the bearing outer ring. However, a plurality of hooks and the grooves each extending for a section of a circumference may be disposed at appropriate intervals along the periphery of the disc or the bearing.

Further, the stationary dust control disc may be attached to the bearing in any suitable manner other than the hook/groove fitting. For example, the stationary disc may directly be fixed on the bearing outer ring with a suitable means such as an adhesive.

The bearings in the preferred embodiments are ball bearings, but a metal bearing may also be used as well.

The discharge ports, which are oriented in parallel to the bur sleeve, may also be directed radially with respect to the bur sleeve, as long as the ports connect the space M to outside.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising:
   a housing having a wall,
   a bur sleeve for receiving and holding a dental tool therein,
   a bearing for rotatably supporting said bur sleeve,
   a rotary dust control member fixed on said bur sleeve, and
   a stationary dust control member forming a gap in cooperation with said rotary dust control member and the wall of the housing for preventing intrusion of contaminants into the housing,
   wherein said stationary dust control member is attached to said bearing.

2. The dental handpiece of claim 1, wherein said bearing has an outer ring, and wherein said stationary dust control member is attached to said outer ring of the bearing.

3. The dental handpiece of claim 1 wherein said stationary dust control member has a hook, and said bearing has a groove, whereby said hook fits in said groove to provide attachment of the stationary dust control member to the bearing.

4. The dental handpiece of claim 3 wherein said stationary dust control member has a radially outer surface, and said bearing includes an outer ring having a radially inner surface, said stationary dust control member having a hook on said radially outer surface, and said bearing having a groove on said radially inner surface of the outer ring.

5. The dental handpiece of claim 3 wherein said stationary dust control member has a radially inner surface, and said bearing includes an outer ring having a radially outer surface, said stationary dust control member having a hook on said radially inner surface, and said bearing having a groove on said radially outer surface of the outer ring.

6. The dental handpiece of claim 1 wherein said stationary dust control member has a groove, and said bearing has a hook, whereby said hook fits in said groove to provide attachment of the stationary dust control member to the bearing.

7. The dental handpiece of claim 6 wherein said stationary dust control member has a radially outer surface, and said bearing includes an outer ring having a radially inner surface, said stationary dust control member having a groove on said radially outer surface, and said bearing having a hook on said radially inner surface of the outer ring.

8. The dental handpiece of claim 6 wherein said stationary dust control member has a radially inner surface, and said bearing includes an outer ring having a radially outer surface, said stationary dust control member having a groove on said radially inner surface, and said bearing having a hook on said radially outer surface of the outer ring.

9. The dental handpiece of claim 1, further comprising:
   a tool insertion port opened at one end of said housing, and
   a discharge port extending through the wall of said housing in the vicinity of the tool insertion port,
   whereby said rotary dust control member and said stationary dust control member cooperate to discharge through said discharge port contaminants entered into the housing.

10. The dental handpiece of claim 9 wherein said discharge port is directed in parallel to the bur sleeve.

* * * * *